United States Patent [19]

Görl

[11] 4,413,279

[45] Nov. 1, 1983

[54] METHOD FOR CONTACT-FREE DETERMINATION OF QUALITY FEATURES OF A TEST SUBJECT OF THE MEAT GOODS CLASS

[75] Inventor: Reinhard Görl, Neusass, Fed. Rep. of Germany

[73] Assignee: Pfister GmbH, Fed. Rep. of Germany

[21] Appl. No.: 330,935

[22] Filed: Dec. 15, 1981

[30] Foreign Application Priority Data

Dec. 17, 1980 [DE] Fed. Rep. of Germany ....... 3047490

[51] Int. Cl.³ ............................................. H04N 7/18
[52] U.S. Cl. .................................. 358/107; 356/445; 356/237; 358/106
[58] Field of Search ............... 358/106, 107, 284, 282; 356/445, 237

[56] References Cited

U.S. PATENT DOCUMENTS 3,443,026  5/1969  Townsend ........................... 358/282
4,226,540 10/1980  Barten et al. ....................... 356/445
4,327,375  4/1982  Le Clerc ............................. 358/107

Primary Examiner—Joseph A. Orsino, Jr.
Attorney, Agent, or Firm—Hill, Van Santen, Steadman & Simpson

[57] ABSTRACT

A method for contact-free determination of quality features of a meat goods test subject provides for determination of a proportional fat-meat ratio of a carcass half. The test subject is illuminated and scanned by a video camera with the meat and fat tissues being distinguished from one another according to relative brightness. Brightness signals from the camera are digitized by comparing the brightness signals with a discrimination-typical threshold value corresponding to a brightness determined such that all brighter and all darker tissue parts respectively deviating above and below the threshold value are represented as white or approximately white image parts and as black or approximately black image parts. The discrimination-typical threshold value is established as a value which is substantially independent of a background brightness associated with the test subject so as to solely distinguish between brightness signals of the meat tissue only.

10 Claims, 3 Drawing Figures

SCANNED IMAGE LOCATION

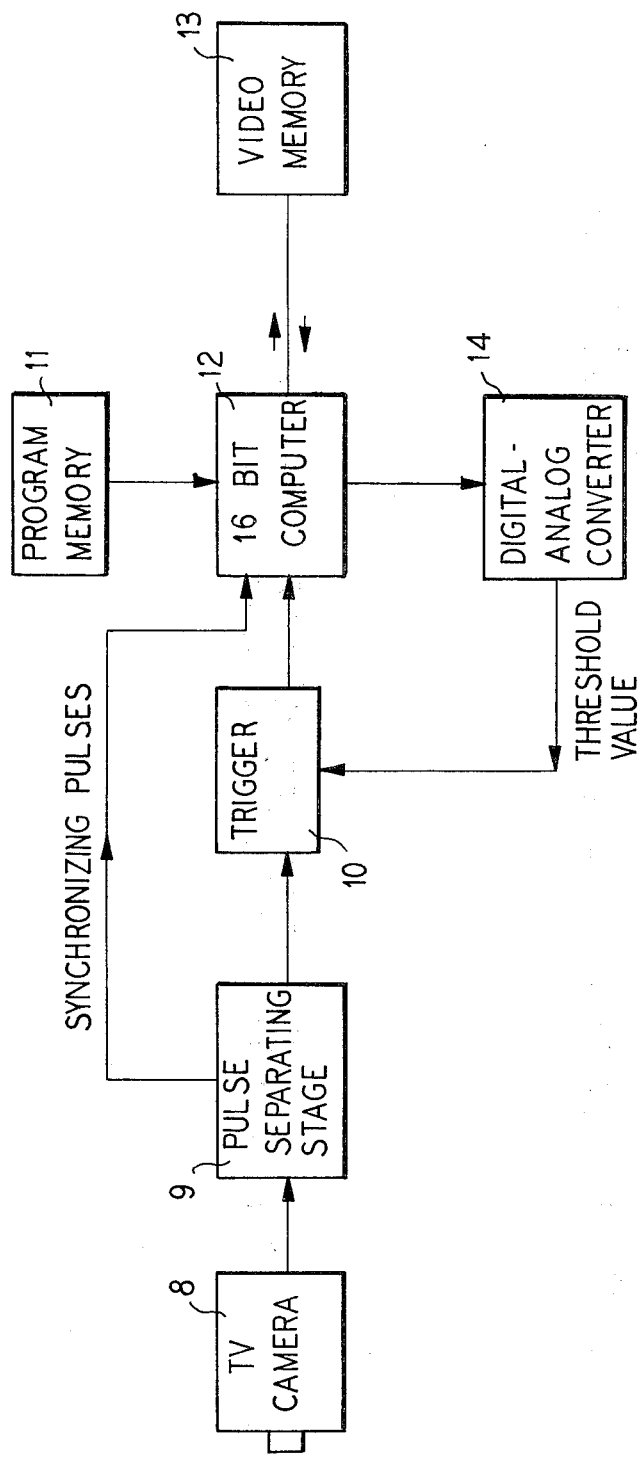

METHOD FOR CONTACT-FREE DETERMINATION OF QUALITY FEATURES OF A TEST SUBJECT OF THE MEAT GOODS CLASS

BACKGROUND OF THE INVENTION

The invention relates to a method for contact-free determination of quality features of a test subject of the meat goods class, particularly for the determination of the proportional fat/meat ratio of a half carcass. The test subject is illuminated and its image is scanned or detected by a video camera. The meat or fat tissue is discriminated according to the measure of the relative brightness of the corresponding tissue parts.

A method of this general type is known from U.S. Pat. No. 4,226,540, incorporated herein by reference. In this method, the real image of a sample scanned by a video camera is digitized relative to a threshold value for the discrimination of fat and meat. This threshold value corresponds to the mean brightness value between the brightest and darkest image locations. Although usable results have often been achieved with the known method, erroneous results cannot be excluded and are particularly produced by the following causes:

indistinct transitions from fat to meat and vice versa in a broad spectrum of gray scales of the real image;

differing colorations of different tissue types in meat, for example muscle tissue and connective tissue;

contaminations of the fatty cut surfaces, for example due to deficient draining of the blood when the carcass is split;

hemorrhages embedded in the loin fat which are caused by blows;

discolorations of skin areas when cooling the carcass;

camera instabilities with a tolerance range, for example in the aperture setting, displacement of the white sensitivity due to voltage decompensations and the like;

illumination instabilities; and non-linear behavior of the image analysis in the computer.

The overall influence of these errors has led, in certain instances, to errors in the digitization, whereby particularly in the indistinct transitions from fat to meat, fat components were reproduced as meat or meat components were reproduced as fat.

SUMMARY OF THE INVENTION

An object of the invention consists of improving the known method in such manner that the perceived difficulties are overcome. In particular, distinguishing features for fat and meat should be reliably perceived with the improved method even when, as a result of the aggravating conditions which have been described above, such features can only be unclearly perceived given an indistinct transition from fat to meat. Accordingly, the recognition quality of the video-optical means should be sensitized by means of an improved method to such a degree that it approximately corresponds to the perception and discrimination capability of the human eye. Apart from the insufficiencies to be attributed to the condition of the sample, those errors are particularly to be eliminated which are attributable to illumination instabilities as well as, under certain conditions, deficiencies in setting or conversion of the camera device.

The object is achieved by digitizing the observed real image of the sample by reference or comparison to a discrimination-typical or specific threshold value of such a brightness that all brighter or darker tissue parts which deviate from the threshold value are represented as white or nearly white image parts or as black or nearly black image parts and vice versa.

For explanation purposes, it should be noted here that what is meant in this invention by digitization of the real image is a processing of the brightness values of the image in which brightness values or gray scales blending into one another are sharply delimited from one another at a specific threshold value by fixing an upper and/or a lower brightness threshold. Thus, it is a matter of editing the real image, which is originally composed of an analog sequence of gray scales of a gray scale spectrum from bright to dark, into a binary image statement in which all brightness values below a randomly fixed brightness threshold appear as black or, in an inverse method, as white; and all brightness values above the brightness threshold appear as white or, respectively, in an inverse method, as black. As a final consequence, the digitized image no longer contains any gray tones, but only substantially black or white image parts. Accordingly, the advantage arises with the invention that by means of introducing a discrimination-typical or specific threshold value which is different for each sample under consideration, the separating line for the precise recognition of the tissue types to be discriminated is placed at a brightness level which still yields perceptible features for these tissue types, even under the most unfavorable conditions.

In a development of the method of the invention, the discrimination-typical or specific threshold value is selected in such manner that all brighter tissue parts are assigned to the fatty tissue and all darker tissue parts are assigned to the meat tissue.

The advantage which arises is that the unclear areas present in the sample, such as contaminations of the fatty cut surfaces by blood or hemorrhaging in the loin fat or different brightness values in the meat, etc., no longer lead to evaluation errors since by use of the discrimination-specific threshold value, a correct digitization for sharp contrasting is also made possible even for the inherently indistinct sample parts proceeding from the gray zones. Likewise, illumination instabilities or sensitivity shifts in the camera and in the transmission system are compensated.

In a further development of the method of the invention, the determination of the discrimination-typical threshold value is carried out according to the following steps:

(a) The sample is optically scanned line and imagewise against a dark background with a black-white camera, and a sharply emerging contour which arises at the brightness transition background/sample, is recorded and/or stored as a skip or step function on a brightness/image location x/y graph or diagram with the step function being parallel to the brightness Y-axis.

(b) Brightness values of the brightest part "$P_h$" and of the darkest part "$P_d$" are determined from the image components at both sides of the step function and are converted into numerical values in accordance with the brightness scale on the Y-axis. From these numerical values a first threshold value of the brightness "$S_1$" is calculated according to the equation $$S_1 = 0.5 \times (P_h + P_d).$$

(c) The calculated first threshold value $S_1$ is shifted up in the direction of increasing brightness at the Y-axis until the skip or step function changes into a finite function $y = n \, x$ due to a deviation or inclination from the vertical direction.

(d) The real image is digitized into the black-white image with the new threshold value of the brightness "$S_2$" thereby determined.

By means of the determination of the discrimination-specific threshold value, the discrimination limit of the various tissue types is lifted to that brightness level from which a high-contrast discrimination of the individual tissue parts is reliably possible while avoiding the sources of error cited above.

Accordingly one can proceed in such manner that the shift of the threshold value in the direction of increasing brightness is undertaken by means of readjusting the aperture of the camera in the closing direction. By so doing, the indistinct range within the gray zones is shifted to a range of greater discrimination by means of darkening such gray zones which originally were in a brighter range.

The same effect can be achieved to shift the threshold value in the direction of increasing brightness by means of corresponding voltage changes in the comparator of the video camera and, finally, an identical effect in the shift of the threshold value in the direction of increasing brightness can be undertaken by means of reducing the illumination intensity of the observed image.

BRIEF DESCRIPTION OF THE DRAWINGS

FIG. 3 is a block digram illustrating a preferred embodiment of the apparatus employed to create and analyze the brightness profile.

DESCRIPTION OF THE PREFERRED EMBODIMENTS

Figure 1:
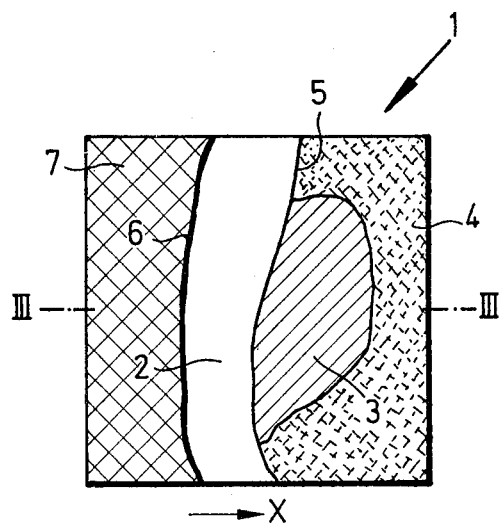
FIG. 1 is a greatly simplified real image of the video camera of the loin fat of a carcass half.

Greatly simplified, FIG. 1 shows the real image 1 of the loin section of a carcass half with a layer 2 of loin fat, a somewhat darker layer 4 of fatty tissue and, enclosed between them, a section of muscle tissue 3. The representation of the real image 1 ensues against a dark background 7, in comparison to which the body edge 6 of the real image 1 emerges with a sharp profile at the limit of the fatty layer 2. A second contour 5 is produced at the boundary line between fat 2 and meat 3 on the one hand and fat 2 and fat-permeated tissue 4 on the other hand.

Figure 2:
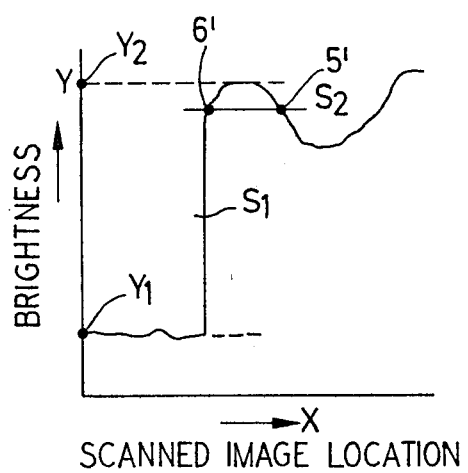
FIG. 2 illustrates the brightness profile along the section line III—III in FIG. 1.

FIG. 2 shows the brightness profile at the section line III—III in FIG. 1. Here, $Y_1$ indicates the lower brightness value as a product of the dark tone of the background 7 and the so-called dark current of the camera. A skip or step function "F" in the brightness curve is produced at the body edge 6 between the dark background 7 and the layer 2 of loin fat, the body edge 6 being sharply imaged with said skip or step function "F" at the dark background 7 by the camera lens. Accordingly, the edge of the contour at the body edge 6 has a finite rise composed of band widths and image focus, but this is so slight that it plays no part in the image evaluation. When, therefore, the contour at the body edge 6 is formed with the threshold $S_1$ according to the equation $$S_1 = 0.5 \times (Y_1 + Y_2),$$

then a sharp discrimination line would result for the bright/dark transitions of the body edge 6 at the dark background 7 but not for the areas of indistinct gray tones, for example at transitions from brighter meat areas into contaminated areas of fatty tissue. Therefore, the original threshold value $S_1$ is shifted upwardly with the features of shifting in the direction of increasing brightness disclosed in the invention (i.e. in the direction of the arrow of the Y-axis in FIG. 2) until, at the threshold value $S_2$, the skip or step function changes into a slope at 6' (the body edge) and begins to shift parallel toward the right in the X-direction with a slight rounding in the brightness curve. This is the indication that the discrimination-specific threshold value $S_2$ has been reached at which the boundary line represented by 5' obliterated with a broad spectrum of mutually bleeding gray tones is imaged relatively sharply.

When the real image 1 is now digitized with the newly gained discrimination-specific threshold value $S_2$, all darker tones, for example gray tones, appear black and all brighter tones, for example gray tones appear white. And given an inverse method, all brighter tones appear black and all darker tones appear white. Given this formation of the threshold value, all error sources which were initially cited and are presently known are eliminated. Misadjustments of the camera brightness sensitivity level or the illumination intensity can likewise no longer influence the contrast sharpness of the image, since the method with the discrimination-typical threshold value $S_2$ either supplies proper image information or no image information.

A preferred embodiment of an apparatus for analysis of the brightness curve shown in FIG. 2 and for setting the threshold value $S_2$ is shown in FIG. 3. The system consists of a normal continuously operating television camera 8 as well as a trigger circuit 10 whose threshold value can be adjusted over the total dynamic range of the video signal, that is from 0 to 1.5 volts. In between there lies a pulse separating stage 9 which has the task of separating the synchronizing pulses from the picture content. For processing of the picture information, the arrangement also has a 16 bit computer 12 with program memory 11 and video memory 13 as well as a digital-analog converter 14.

The manner of operation is as follows. The camera 8 sees the picture section of a body according to FIG. 1. This picture section consists of the dark background 7 and the bright body which is composed of fat 2, meat 3, and connective tissue portions. In FIG. 2, the relative brightness values of a line of this picture section are represented. One sees that the dark background beginning with $Y_1$ is to have a significantly lesser brightness and thus a lesser video level than the body portion beginning at the step function with 6'. At a random point in time, the computer 12 obtains the command from the program stored in 11 to evaluate a picture. Now, the computer 12 outputs a digit lying between 0 and 255, synchronized with a camera picture change, into the digital-analog converter 14 which converts this into a proportional analog value between 0 and 1.5 volts and places it at the trigger 10 as a threshold value. From this point in time on, all picture points which are larger than the threshold value are written into the video memory 13 via the computer 12 by the trigger 10 as a high level and all picture points lying lower are written in by the trigger as a low level. After an iterative procedure, in order not to have to pass through all of the 256 (0+255) gray stages, the computer 12 reduces the threshold value until all picture points of the total picture comprised of the body plus background are displayed white or, respectively, as a high level. The computer 12 notes this threshold value, let it for example be 62. Now the threshold value is raised iteratively until all picture points of the picture (body+background) are written into the memory as a low level, in other words as dark data points. Let this value, for example, be 154. The computer from this calculates the arithmetic mean (154+62)/2=108 and provides this threshold value to the digital-analog converter 14. This corresponds in FIG. 2 to the value $S_1$. One sees that now only the background 7 lies below this threshold value, while the brightness of the body, whether meat, fat, or connective tissue, is larger. The picture now written into the video memory contains per line a black-white or, respectively, low-high transition, namely where the background to body transition occurs. These transitions from low to high of all lines stored as image point location coordinates (line number/column number) characterize precisely the location of the leading edge of the carcass of the slaughtered animal.

Proceeding from this value 108 or respectively $S_1$ in FIG. 2, now the threshold value is raised in steps and after each step the background/body transition 6 in FIG. 1 is determined and is stored with the stored boundary 6 in FIG. 1. As long as the threshold value is located in the steep region between background and body, the boundary limit 6 in FIG. 1 does not change or changes only a little with respect to that determined with the threshold value 108.

As FIG. 2 shows, however, the brightness profile of the body beginning from 6' is rounded. Accordingly, when the threshold value is increased step-by-step up to threshold $S_2$ so that the point 6' is reached, the position coordinates of the leading edge now found no longer agree with those found at the setting 108. In act, they are all positioned to the right, more or less, in parallel fashion. This criterion or comparison indicates to the computer 12 that the adjustment sought for the picture evaluation at which the critical transition from fat 2 to meat 3 is correctly reproduced at point 5' has been found.

Although various minor modifications may be suggested by those versed in the art, it should be understood that I wish to embody within the scope of the patent warranted hereon, all such embodiments as reasonably and properly come within the scope of my contribution to the art.

I claim as my invention:

1. A method for contact-free determination of quality features of a meat goods test subject by determining a proportional fat-meat ratio of a carcass half, comprising the steps of: illuminating the test subject and scanning its image by a video camera, the meat tissue and fat tissue being distinguished from one another according to a measure of relative brightness of the corresponding tissues; digitizing brightness signals created by the camera observing the image of the sample by comparing the brightness signals with a discrimination-typical threshold value corresponding to a brightness determined such that all brighter and all darker tissue parts respectively deviating above and below the threshold value are represented as white or approximately white image parts and as black or approximately black image parts; establishing the discrimination-typical threshold value as a value which is substantially independent of a background brightness associated with the test subject and so as to solely distinguish between brightness signals of the meat tissue only; and the establishment of the discrimination-typical threshold value is carried out in the following steps (a) optically scanning the sample linewise with a black-white camera against a dark background and storing a sharply emerging contour thereby arising at a brightness transition from background to sample as a vertical line forming a step function defined in a brightness verses image location x/y diagram and where said step function lies parallel to the Y-axis plotting brightness;

(b) brightness values of the brightest part "$P_h$" and of the darkest part "$P_d$" are determined from image points at both ends of the step function and are converted into numerical values according to the brightness scale at the Y-axis, and calculating from these numerical values a first threshold value of the brightness "$S_1$" according to the equation $$S_1 = 0.5 \times (P_h + P_d);$$

(c) shifting the calculated first threshold value $S_1$ in a direction of increasing brightness along the Y-axis until the step function changes into a finite function $y = n\,x$ due to sloping of the brightness curve away from the vertical; and (d) digitizing the real image into a black-white image by use of the newly established threshold value of the brightness.

2. A method according to claim 1 wherein the discrimination-typical threshold value is selected in such manner that all brighter tissue parts are allocated to the fatty tissue and all darker tissue parts are allocated to the meat tissue.

3. A method according to claim 1 wherein the step of shifting the threshold value in the direction of increasing brightness is undertaken by means of readjusting an aperture of the camera in a closing direction.

4. A method according to claim 1 wherein the step of shifting the threshold value in the direction of increasing brightness is undertaken by means of a voltage change in a comparator of the video camera.

5. A method according to claim 1 wherein the step of shifting threshold value in the direction of increasing brightness is undertaken by means of reducing an illumination intensity of the observed image.

6. A method for contact-free determination of quality features of a meat goods test subject by determining a fat-meat tissue ratio of a carcass, comprising the steps of: illuminating the test subject such that the meat tissue and fat tissue create areas of differing brightness corresponding to the amount of meat or fat present, and scanning an image of the test subject by a video camera along a given line which begins at a background area and proceeds to a boundary of test subject with background, and then inwardly over the test subject; storing the resulting brightness signals from the camera; determining a first threshold value as an average value $(P_h + P_d)/2$ between a brightest picture part "$P_h$" and a darkest picture part "$P_d$" from the brightness signals of the scanned image; shifting the calculated first threshold value up in a direction of increasing brightness along a step function portion of a brightness curve formed by plotting brightness signal level verses scanned image location, the step function formed as a vertical line parallel to a brightness Y-axis of the plot and arising from scanning the boundary between the test subject and the background, the threshold value being shifted up until the brightness curve changes into a finite function formed by a sloping portion of the brightness curve away from the vertical axis; and digitizing the real image into a black-white image by use of the newly determined discrimination-specific threshold value of the brightness, all stored brightness signals being catergorized as either black or white depending upon whether they are above or below the discrimination-specific threshold value.

7. A method according to claim 6 wherein the step of shifting the threshold value in the direction of increasing brightness is undertaken by means of readjusting an aperture of the camera in a closing direction.

8. A method according to claim 6 wherein the step of shifting the threshold value in the direction of increasing brightness is undertaken by means of a voltage change in a comparator of the video camera.

9. A method according to claim 6 wherein the step of shifting threshold value in the direction of increasing brightness is undertaken by means of reducing an illumination intensity of the observed image.

10. A method according to claim 6 wherein the discrimination-specific threshold value is selected in such manner that all brighter tissue parts are allocated to the fatty tissue and all darker tissue parts are allocated to the meat tissue.

* * * * *